(12) United States Patent
He et al.

(10) Patent No.: US 11,965,875 B2
(45) Date of Patent: Apr. 23, 2024

(54) SYSTEM AND METHOD FOR SCREENING AND ASSESSING AGENTS FOR TUMOR IMMUNOTHERAPY

(71) Applicant: ADLAI NORTYE BIOPHARMA CO., LTD., Hangzhou (CN)

(72) Inventors: Nanhai He, Hangzhou (CN); Youping Wang, Hangzhou (CN); Yang Lu, Hangzhou (CN); Donghui Yang, Hangzhou (CN)

(73) Assignee: ADLAI NORTYE BIOPHARMA CO. LTD., Hangzhou (CN)

( * ) Notice: Subject to any disclaimer, the term of this patent is extended or adjusted under 35 U.S.C. 154(b) by 364 days.

(21) Appl. No.: 17/323,078

(22) Filed: May 18, 2021

(65) Prior Publication Data
US 2022/0155282 A1  May 19, 2022

(30) Foreign Application Priority Data

Nov. 17, 2020 (CN) .................. 202011284771.X (51) Int. Cl.
*C12N 5/00* (2006.01)
*G01N 33/50* (2006.01)

(52) U.S. Cl.
CPC ....... *G01N 33/5011* (2013.01); *G01N 33/505* (2013.01); *G01N 33/5052* (2013.01)

(58) Field of Classification Search
CPC .................................................. G01N 33/5011
See application file for complete search history.

(56) References Cited

FOREIGN PATENT DOCUMENTS

| CN | 106957893 A | 7/2017 |
|----|-------------|--------|
| WO | 2017113444 A1 | 7/2017 |

OTHER PUBLICATIONS

EP 21173085.8 Extended European Search Report dated Nov. 12, 2021.
Adlai, et al., Paint-2DTM Platform for Immune Therapeutics discovery and Development, XP055854728, Retrieved from the internet: url:https://en.adlainortye.com/index.pho/technology; Feb. 28, 2021.
Appleton, Kathryn M., et al., Abstract 500: Predicting patient response to immuno-oncology agents in vitro using 3D cultures, Immunology, Am. Assoc. for Cancer Research, AACR Annual Meeting 2019, vol. 79 (13 Suppl. S), Jul. 1, 2019.
Appleton, Kathryn M., et al., Abstract 2244: PARP inhibition in combination with pembrolizumab enhances cytotoxicity in ovarian cancer patient-derived 3D spheroids, Am. Assoc. for Cancer Research, Annual Meeting, AACR 2020, vol. 80 (16 Suppl.) Aug. 1, 2020.
Cong, Ye, et al., Drug Toxicity Evalution Based on Organ-on-a-chip Technology: A Review, Micromachines, vol. 11, 381, No. 4, Apr. 3, 2020.
Lassahn, Katy A., et al., Abstract 315: Multifaceted functional assessment of checkpoint inhibitor efficacy using 3D tumor spheroids, Am. Assoc. for Cancer Research Annual Meeting, AACR 2020, vol. 80 (16 Suppl.) Aug. 15, 2020.
Morello, Aurore, et al., P256 A novel bifunctional anti-PD-1/IL-7 fusion protein potentiatesexhausted T cell and disarms Treg suppressive activity, J for ImmunoTherapy of Cancer, vol. 7. No. Suppl 1, 282, Nov. 1, 2019.

*Primary Examiner* — Albert M Navarro
(74) *Attorney, Agent, or Firm* — Honigman LLP; Thomas A. Wootton, Esq.; Jonathan P. O'Brien (57) ABSTRACT

The present application relates to a system and a method for effectively screening and assessing agents for tumor immunotherapy, which includes assessment for the effects of target cells, non-target cells, and tumor infiltration. The system and method of the present application can be used to comprehensively and systematically assess the effectiveness and safety of the agent against tumor immune cells.

9 Claims, 3 Drawing Sheets

SYSTEM AND METHOD FOR SCREENING AND ASSESSING AGENTS FOR TUMOR IMMUNOTHERAPY

This application claims priority under 35 U.S.C. § 119, which claims the benefit of Paris Convention application CN202011284771X, filed Nov. 17, 2020. Priority is claimed to this application and the disclosure of this prior application is considered part of the disclosure of this application and to the extent allowed the entire contents of the aforementioned application is incorporated herein.

TECHNICAL FIELD

The present application relates to the field of biomedicine, in particular to a system and a method for screening and assessing agents for tumor immunotherapy.

BACKGROUND OF THE INVENTION

Tumor immunotherapy refers to a therapeutic method for correcting and maintaining tumor-immune microcirculation by agents and improving the anti-tumor immune effect of organisms to achieve the effect of controlling and even eliminating tumors. In the research and development of new agents for tumor immunotherapy, effective assessment of the effectiveness and safety of agents is a crucial factor to ensure the successful development of related agents. The effectiveness of related immune cells is specifically assessed mainly according to the expression characteristics of targets in the research and development process of novel conventional agents for tumor immunotherapy. However, the improvement of the anti-tumor immune system is not achieved by only depending on a single type of cells, but is achieved by the cooperation of multiple immune cells; however, when using agents for tumor immunotherapy for treatment, the agents inevitably act on other non-target immune cells in addition to target-associated immune cells when exerting their effects, and if such effects would hinder the normal functions of other immune cells, even if the agents show better effects in target-associated immune cells, the anti-tumor immune system would be greatly likely to be unable to be effectively improved, failing to achieve the desired effects by tumor immunotherapy. However, the conventional research and development links of new agents for tumor immunotherapy lack an effective method to avoid the effects of agents, so that the research and development risks of the new agents are increased.

Accordingly, there is a need in the art for an effective system and method for screening and assessing agents for tumor immunotherapy to comprehensively and systematically assess the effectiveness and safety of the agents against tumor immune cells.

SUMMARY OF THE INVENTION

The present application provides an effective system and method for screening and assessing agents for tumor immunotherapy to comprehensively and systematically assess the effectiveness and safety of the agents against tumor immune cells.

In a first aspect, the present application provides a method of assessing the effect of an analyte on tumor immune cells including the steps of: i) assessing the effect of the analyte on target cells, ii) assessing the effect of the analyte on non-target cells; and iii) assessing the effect of the analyte on tumor immune infiltration; where step i) includes: i-1) assessing the effect of the analyte on immune cell line target cells, and i-2) assessing the effect of the analyte on primary immune cell target cells; where after the assessment of step i-1), the assessment result is divided into two levels of positive (+) and negative (−), and the analyte with a negative assessment result is directly determined as a negative analyte without performing any subsequent steps.

In a specific embodiment, the step i-2) is continued for the analyte with a positive assessment result in the step i-1), and the assessment result is divided into two levels of positive (+) or negative (−) using a dual-level system.

In a specific embodiment, the analyte with a negative assessment result in step i-2) is directly determined as a negative analyte without performing any subsequent steps.

In a specific embodiment, where after the assessment of step iii), the assessment result is recorded as a multi-interval scoring level index.

In a specific embodiment, where step ii) includes assessing the effect of the analyte on immune cell line non-target cells, and/or assessing the effect of the analyte on primary immune cell non-target cells.

In a specific embodiment, where after the assessment of step iii), the assessment result is recorded as a multi-interval scoring level index.

In a specific embodiment, where the step iii) includes: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of natural killer cells (NK cells) in tumor tissue.

In a specific embodiment, where the phenotype of T cells includes: a ratio of the T cells in tumor tissue, the proliferative capacity of the T cells, the activity of the T cells, the expression level of interleukin-2 (IL-2) in the T cells, the expression level of tumor necrosis factor α (TNFα) in the T cells, the expression level of granzyme in the T cells, the expression level of interferon-γ (IFNγ) in the T cells, and/or the expression level of programmed death receptor-1 (PD1) in the T cells.

In a specific embodiment, where the phenotype of dendritic cells includes: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

In a specific embodiment, where the phenotype of NK cells includes: a ratio of the NK cells in tumor tissue, the proliferative capacity of the NK cells, the activity of the NK cells, the expression level of C-type lectin receptor family member A (NKG2A) in the NK cells, the expression level of granzyme in the NK cells, and/or the expression level of killer cell immunoglobulin-like receptor KIR in the NK cells.

In a specific embodiment, where the phenotype of macrophages includes: a ratio of the macrophages in tumor tissue, the proliferative capacity of the macrophages, the activity of the macrophages, and/or a ratio of M1-type macrophages to M2-type macrophages in tumor tissue.

In a second aspect, the present application provides a method of assessing the effect of an analyte on tumor immune B cells including the steps of: a) assessing the effect of the analyte on B cells, b) assessing the effect of the analyte on non-target cells; and c) assessing the effect of the analyte on tumor immune infiltration; where step a) includes:

a-1) assessing the effect of the analyte on B cells of an immune cell line, and a-2) assessing the effect of the analyte on B cells of primary immune cells;

where the assessment result is divided into two levels of positive (+) and negative (−), and the analyte with a negative assessment result is directly determined as a negative analyte without performing any subsequent steps.

In a specific embodiment, where the step a) includes: assessing the effect of the analyte on the proliferative capacity of the B cells, assessing the effect of the analyte on the expression level of IL-6 in the B cells, and/or assessing the effect of the analyte on the level of antibody produced by the B cells.

In a specific embodiment, where the non-target cells include T cells, macrophages, dendritic cells, and/or NK cells.

In a specific embodiment, where the step b) includes: assessing the effect of the analyte on the phenotype of T cells, assessing the effect of the analyte on the phenotype of dendritic cells, assessing the effect of the analyte on the phenotype of macrophages, and/or assessing the effect of the analyte on the phenotype of NK cells.

In a specific embodiment, where the phenotype of T cells includes: the expression level of cytokine IL-2 in the T cell, the expression level of IFNγ in the T cell, and/or the proliferative capacity of the T cell.

In a specific embodiment, where the phenotype of dendritic cells includes: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells.

In a specific embodiment, where the phenotype of NK cells includes: the proliferative capacity and the activity of the NK cells, the expression level of NKG2A in the NK cells, the expression level of granzyme in the NK cells, and/or the expression level of KIR in the NK cells.

In a specific embodiment, where the phenotype of macrophages includes: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

In a specific embodiment, where the step c) includes: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue.

In a specific embodiment, where the phenotype of T cells includes: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells.

In a specific embodiment, where the phenotype of dendritic cells includes: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

In a specific embodiment, where the phenotype of NK cells includes: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells.

In a specific embodiment, where the phenotype of macrophages includes: a ratio of the macrophages in tumor tissue, the proliferative capacity of the macrophages, the activity of the macrophages, and/or a ratio of M1-type macrophages to M2-type macrophages in tumor tissue.

In a third aspect, the present application provides a method of assessing the effect of an analyte on tumor immune T cells including the steps of: a') assessing the effect of the analyte on T cells, b') assessing the effect of the analyte on non-target cells; and c') assessing the effect of the analyte on tumor immune infiltration;

where the step a') includes:

a-1') assessing the effect of the analyte on T cells of an immune cell line, and a-2') assessing the effect of the analyte on T cells of primary immune cells;

where the assessment result is divided into two levels of positive (+) and negative (−), and the analyte with a negative assessment result is directly determined as a negative analyte without performing any subsequent steps.

In a specific embodiment, where the step a') includes: assessing the effect of the analyte on the expression level of IL-2 in the T cells, assessing the effect of the analyte on the expression level of IFNγ in the T cells, and/or assessing the effect of the analyte on the cell the proliferative capacity of the T cells.

In a specific embodiment, where the non-target cells include B cells, macrophages, dendritic cells, and/or NK cells.

In a specific embodiment, where the step b') includes: assessing the effect of the analyte on the phenotype of B cells, assessing the effect of the analyte on the phenotype of dendritic cells, assessing the effect of the analyte on the phenotype of macrophages, and/or assessing the effect of the analyte on the phenotype of NK cells.

In a specific embodiment, where the phenotype of B cells includes: the proliferative capacity of the B cells, and/or production of antibodies by the B cells.

In a specific embodiment, where the phenotype of dendritic cells includes: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells.

In a specific embodiment, where the phenotype of NK cells includes: the proliferative capacity and the activity of the NK cells, the expression level of NKG2A in the NK cells, the expression level of granzyme in the NK cells, and/or the expression level of KIR in the NK cells.

In a specific embodiment, where the phenotype of macrophages includes: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

In a specific embodiment, where the step c') includes: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue.

In a specific embodiment, where the phenotype of T cells includes: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells.

In a specific embodiment, where the phenotype of dendritic cells includes: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

In a specific embodiment, where the phenotype of NK cells includes: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells.

In a specific embodiment, where the phenotype of macrophages includes: a ratio of the macrophages in tumor tissue, the proliferative capacity of the macrophages, the activity of the macrophages, and/or a ratio of M1-type macrophages to M2-type macrophages in tumor tissue.

In a fourth aspect, the present application provides a system including a test unit, a data acquisition unit, and a data assessment unit; where the test unit includes an immune cell line test module S1, a primary immune cell test module S2 and a tumor-infiltrating immune cell test module S3; the data acquisition unit is configured to independently record the data generated by each module of the test unit respectively; and the data assessment unit is configured to assess the data recorded by the data acquisition unit.

In a specific embodiment, the data assessment unit further includes a filter element configured to filter the analyte in the test unit corresponding to the data based on the assessment of the data.

In a specific embodiment, the immune cell line test module S1 includes an immune cell line target cell test sub-module S1-1 and an immune cell line non-target cell test sub-module S1-2.

In a specific embodiment, the data assessment unit is configured to assess the input data of the sub-module S1-1 recorded by the data acquisition unit, and output an assessment result of a positive (+) or negative (−) level.

In a specific embodiment, the filter element is configured to remove the analyte corresponding to the data with a negative assessment result of the sub-module S1-1 from the test unit.

In a specific embodiment, the primary immune cell test module S2 includes a primary immune cell target cell test sub-module S2-1 and a primary immune cell non-target cell test sub-module S2-2.

In a specific embodiment, the data assessment unit is configured to assess the input data of the sub-module S2-1 recorded by the data acquisition unit, and output an assessment result of a positive (+) or negative (−) level.

In a specific embodiment, the filter element is configured to remove the analyte corresponding to the data with a negative assessment result of the sub-module S2-1 from the test unit.

In a specific embodiment, the data assessment unit is configured to assess the data of the module S1, the data of the module S2, and the data of the module S3 recorded by the input data acquisition unit, and output a multi-interval scoring level index.

In a specific embodiment, the data assessment unit is configured to assess and predict an agent development risk based on the level index.

In a fifth aspect, the present application provides use of the system according to the fourth aspect in the preparation of a high throughput screening system of agents for tumor immunotherapy.

In a sixth aspect, the present application provides a method of assessing the effectiveness and/or safety of a tumor immunotherapeutic agent against tumor immune cells, including using the system according to the fourth aspect. The data assessment unit is configured to assess and predict an agent development risk based on the level division.

Other aspects and advantages of the present application will become readily apparent to those skilled in the art from the following detailed description. Only exemplary embodiments of the present application are shown and described in the following detailed description. As will be recognized by those skilled in the art, the contents of this application enable those skilled in the art to make modifications to the specific embodiments disclosed without departing from the spirit and scope of the present invention to which this application pertains. Accordingly, the drawings and description herein are to be regarded as illustrative, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1:
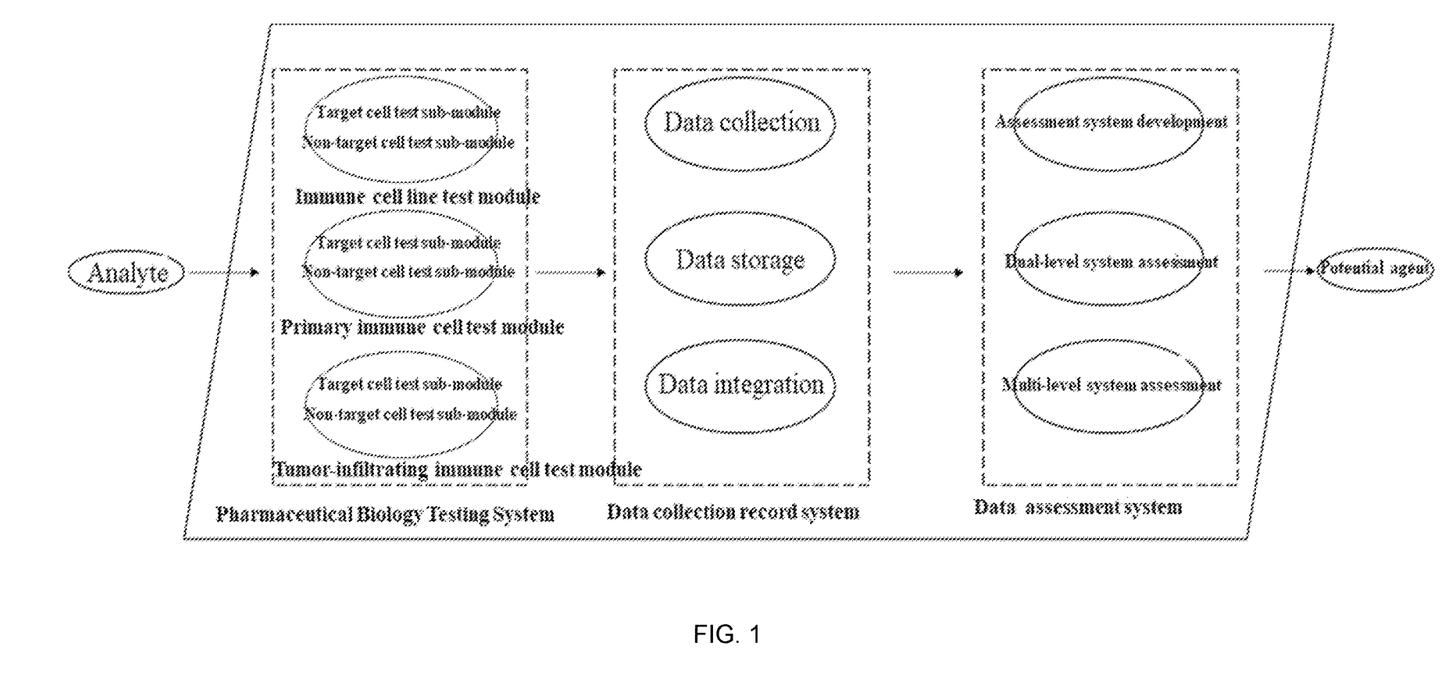
FIG. 1 shows a schematic diagram of a system of agents for tumor immunotherapy described herein.
Figure 2:
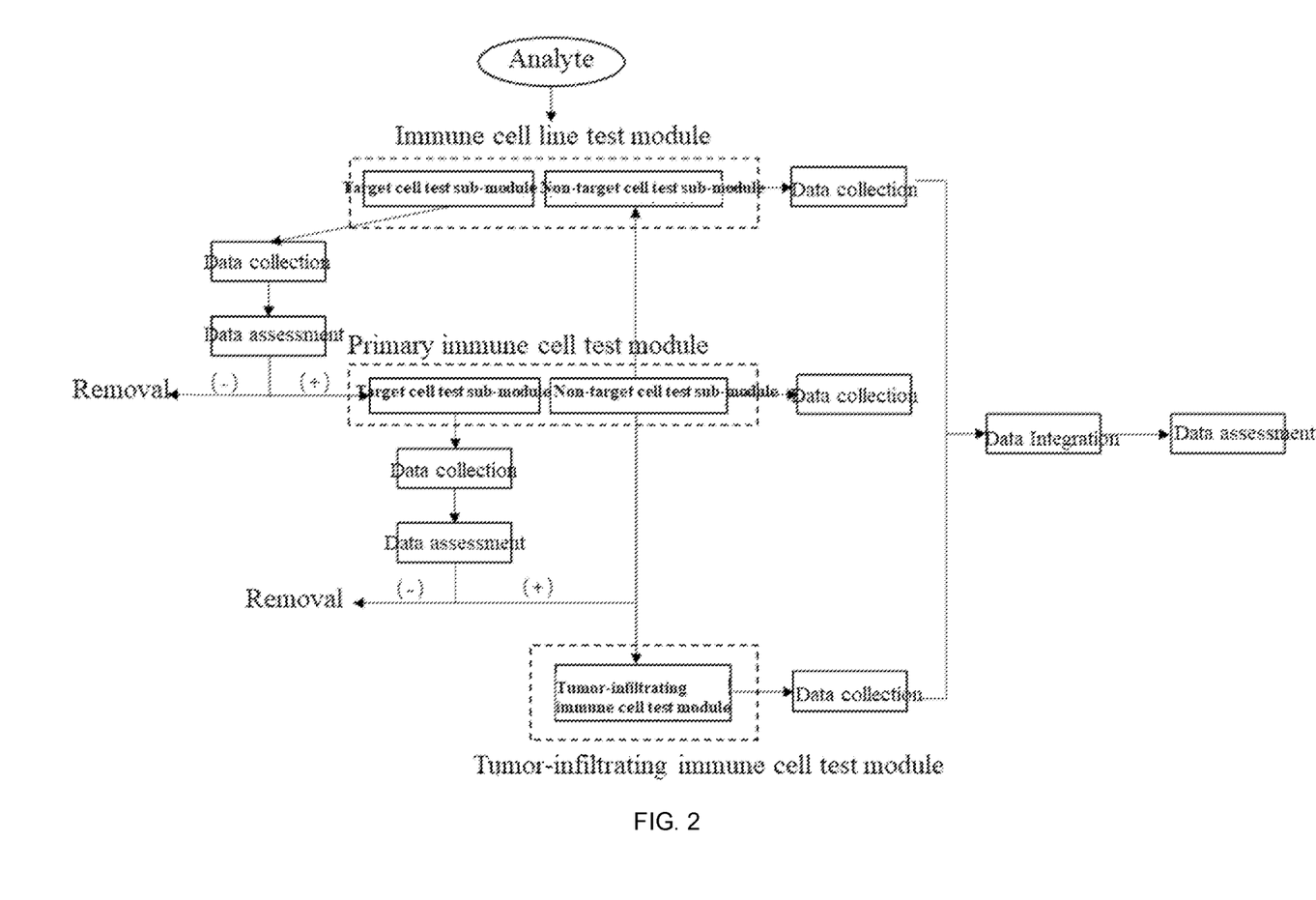
FIG. 2 shows a flow chart of assessment of an analyte using the system of agents for tumor immunotherapy as described herein.
Figure 3:
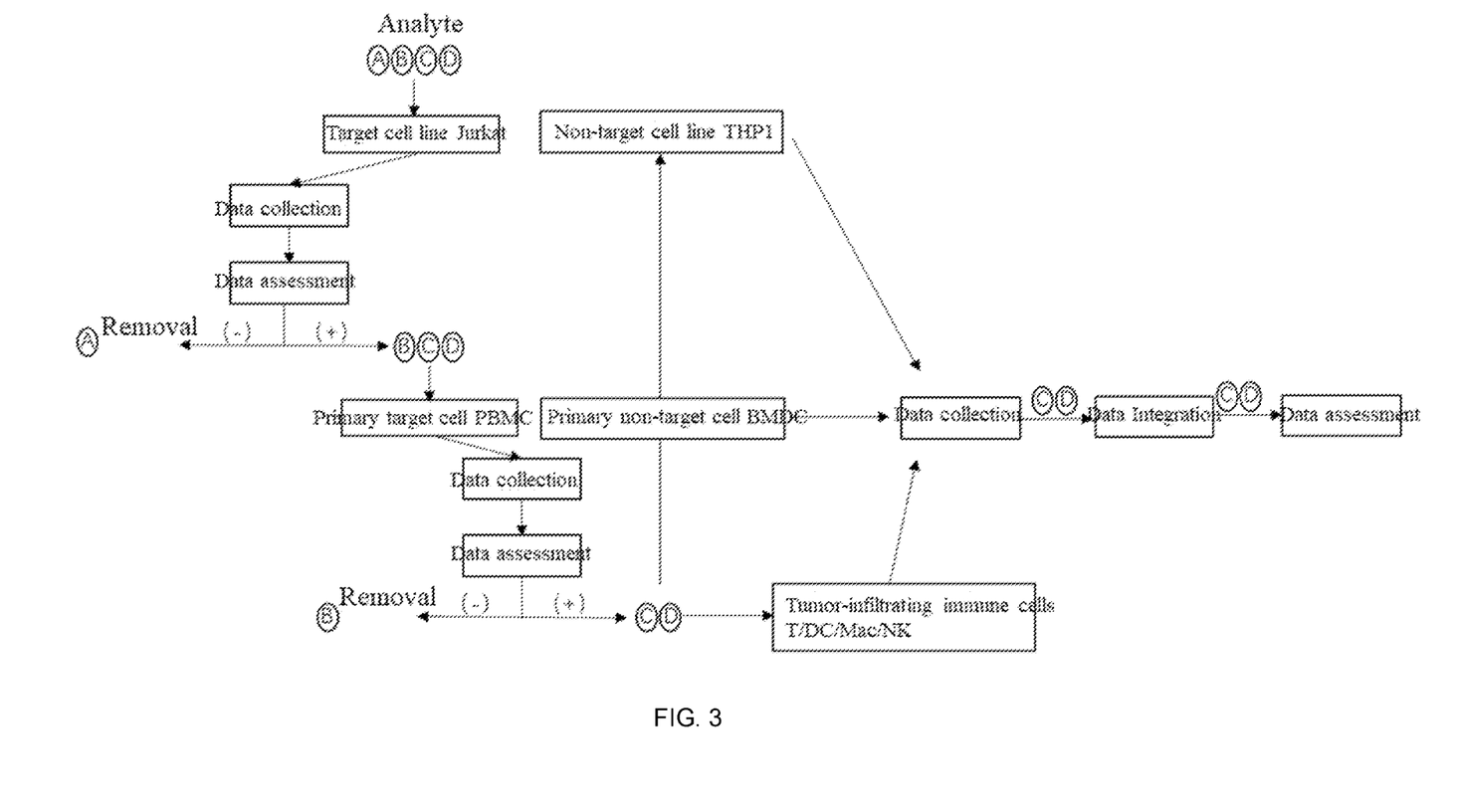
FIG. 3 shows an example of assessment of an analyte using the system of agents for tumor immunotherapy as described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Other advantages and effects of the present invention will become readily apparent to those skilled in the art from the following description of specific embodiments.

Definition of Terms

In this application, the term "tumor immunity" may generally include the effects of the body on tumor antigens, immune cell-associated tumor cell escape, and changes in the phenotype of immune cells during occurrence, development, and metastasis of the tumor. The tumor immunity may generally include tumor-associated cellular and humoral immunity. For example, the effect of the analyte described herein on tumor immune cells may be embodied by the phenotype of the target cells, the phenotype of the non-target cells, and the phenotype of each immune cell in the tumor tissue in the presence of the analyte.

As used herein, the terms "target cells" and "target-associated cells" are used interchangeably and generally refer to the target cells, or the cells of interest. In the presence of an analyte, the target cell may exhibit certain changes and thus may serve as a test subject reflecting the performance of the analyte. As used herein, the term "non-target cells" generally refers to cells that are not targeted. The non-target cells may also exhibit certain changes in the presence of the analyte. In the present application, the target cells and non-target cells may be derived from cell lines or primary cells. For example, the target cells and non-target cells may be immune cell lines or primary immune cells. The target cell is generally a type of immune cell, and in particular, the target cell may be a plurality of immune cells.

As used herein, the term "immune cells" generally refers to cells involved in an immune response, e.g., promoting an immune response. Examples of immune cells include lymphocytes, such as B cells and T cells; natural killer cells; myeloid cells such as monocytes, macrophages, eosinophils, mastocytes, basophils, and granulocytes.

As used herein, the term "tumor immune cells" generally refers to immune cells associated with tumor immunity.

As used herein, the term "cell lines" generally refers to immortalized cell clones. Under suitable conditions, cell lines can be multiplied for generations in vitro, and the phenotypes of cell lines of each generation are generally consistent; but there may also be some differences.

As used herein, the term "primary cells" generally refers to cells obtained directly from living tissue and cultured in vitro. The primary cells may serve as a model of cells in vivo.

As used herein, the term "phenotype" generally refers to a detectable characteristic exhibited by a cell. The phenotype may be an appearance aspect or a functional aspect. In the present application, the phenotype may be embodied in terms of viability, the proliferative capacity, activation level, or differentiation direction of cells, also in terms of secretion level of cytokines, or in terms of the expression level of other proteins such as cell surface receptors, and co-stimulatory molecules.

In this application, the terms "tumor immune infiltration effect" and "effect on tumor immune infiltration" are used interchangeably and generally refer to the effect of an analyte on tumor-infiltrating lymphocytes. In the present application, the term "tumor-infiltrating lymphocytes" or "TIL" generally refers to a population of cells initially obtained as leukocytes that have exited the bloodstream of the subject and migrated into the tumor. TIL may include, but is not limited to, CD8+ cytotoxic T cells (lymphocytes), Th1 and Th17CD4+ T cells, natural killer cells, dendritic cells, and M1 macrophages.

In this application, the term "module" generally refers to test schemes that run independently of one another, and one module may consist of several sub-modules that are independent of one another and have similar characteristics. Each module may run simultaneously or sequentially; however, where specifically noted, the modules may run in a certain order. For example, in the present application, an analyte may first run an immune cell line target cell test sub-module; the test and assessment of the other modules in the test unit are then performed only when the analyte passes the assessment of the immune cell line target cell test. While the primary immune cell target cell test sub-module, the immune cell line non-target cell test sub-module, the primary immune cell non-target cell test sub-module, and the tumor-infiltrating immune cell test sub-module may run simultaneously or sequentially; they may run in random order, also may run in a predetermined order. For example, the analyte that passes the immune cell line target cell test may be sequentially input into and run the primary immune cell target cell test sub-module, the immune cell line non-target cell test sub-module, the primary immune cell non-target cell test sub-module, and the tumor-infiltrating immune cell test module; or sequentially input into and run the immune cell line non-target cell test sub-module, the primary immune cell target cell test sub-module, the primary immune cell non-target cell test sub-module, and the tumor-infiltrating immune cell test module. Besides, in a specific case, it can be specified that the analyte passing the immune cell line target cell test firstly run the primary immune cell target cell test sub-module, and only the analyte with a positive (+) assessment result may continue to run and be input into the immune cell line non-target cell test sub-module, the primary immune cell non-target cell test sub-module and the tumor-infiltrating immune cell test module in the platform, with the removal of the analyte with a negative (−) assessment result of the primary immune cell target cell test sub-module from the platform; while the immune cell line non-target cell test sub-module, the primary immune cell non-target cell test sub-module, and the tumor-infiltrating immune cell test sub-module may run simultaneously or sequentially; they may run in random order, also may run in a predetermined order.

Detailed Description of the Invention

Assessment Method

The present application provides a method of assessing the effect of an analyte on tumor immune cells including the steps of: i) assessing the effect of the analyte on target cells, ii) assessing the effect of the analyte on non-target cells; and iii) assessing the effect of the analyte on tumor immune infiltration;

where the step i) includes:
i-1) assessing the effect of the analyte on immune cell line target cells, and
i-2) assessing the effect of the analyte on primary immune cell target cells;
where after the assessment of step i-1), the assessment result is divided into two levels of positive (+) and negative (−), and the analyte with a negative assessment result is directly determined as a negative analyte without performing any subsequent steps.

In the present application, an analyte may firstly be assessed for the effect of an immune cell line target cells; the other assessments are then performed only when the analyte passes the assessment for the effect of immune cell line target cells. Subsequently, the effects of primary immune cell target cells, immune cell line non-target cells, primary immune cell non-target cells, and tumor-infiltrating immunity may be assessed simultaneously or sequentially; the above assessments are performed in random order or predetermined order. For example, for the analyte in which the effect of the immune cell line target cell is assessed as positive, the effect of primary immune cell target cells may be assessed firstly, then the effects of immune cell line non-target cells, primary immune cell non-target cells and tumor-infiltrating immune cells may be assessed; subsequently, the effect of immune cell line non-target cells may be assessed firstly, and then the effects of primary immune cell target cells, primary immune cell non-target cells and tumor-infiltrating immune cells may be assessed. Besides, in a specific case, for the analyte in which the effect of the immune cell line target cells is assessed as positive, the effect of primary immune cell target cells may be assessed firstly, where the analyte assessed as negative by the primary immune cell target cells test sub-module is determined as a negative analyte directly without any other assessments, only the analyte with a positive (+) assessment result may continue to assess the effects of immune cell line non-target cells, primary immune cell non-target cells and tumor-infiltrating immune cells; while the assessment for the effects of immune cell line non-target cells, primary immune cell non-target cells and tumor-infiltrating immune cells may be performed simultaneously or sequentially; it may be performed in random order or a predetermined order.

Specifically, when the target cells are B cells, the assessment for the effect of the target cells, i.e., the B cells, may include: assessing the effect of the analyte on the proliferative capacity of the B cells, assessing the effect of the analyte on the expression level of IL-6 in the B cells, and/or assessing the effect of the analyte on the level of antibody produced by the B cells. As for non-target cells, they may include T cells, macrophages, dendritic cells, and/or NK cells. Where the phenotype of T cells may include: the expression level of cytokine IL-2 in the T cell, the expression level of IFNγ in the T cell, and/or the proliferative capacity of the T cell. Where the phenotype of dendritic cells may include: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells. Where the phenotype of NK cells may include: the proliferative capacity and the activity of the NK cells, and the expression level of NKG2A in the NK cells, the expression level of granzyme in the NK cells, and/or the expression level of KIR in the NK cells. Where the phenotype of macrophages may include: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

Specifically, when the target cells are T cells, the assessment for the effect of the target cell, i.e., the T cell, may include: assessing the effect of the analyte on the expression level of IL-2 in the T cells, assessing the effect of the analyte on the expression level of IFNγ in the T cells, and/or assessing the effect of the analyte on the cell the proliferative capacity of the T cells. As for non-target cells, they may include B cells, macrophages, dendritic cells, and/or NK cells. Where the phenotype of B cells may include: the proliferative capacity of the B cells, and/or production of antibodies by the B cells. Where the phenotype of dendritic cells may include: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells. Where the phenotype of NK cells may include: the proliferative capacity and the activity of the NK cells, and the expression level of NKG2A in the NK cells, the expression level of granzyme in the NK cells, and/or the expression level of KIR in the NK cells. Where the phenotype of macrophages may include: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

The target cells may also be macrophages, dendritic cells, and/or NK cells.

The assessment for the effect of tumor infiltration includes the following steps: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue. Where the phenotype of T cells includes: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells in the presence of an analyte. Where the phenotype of dendritic cells includes: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells. Where the phenotype of NK cells includes: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells. Where the phenotype of macrophages includes: a ratio of the macrophages in tumor tissue, the proliferative capacity of the macrophages, the activity of the macrophages, and/or a ratio of M1-type macrophages to M2-type macrophages in tumor tissue.

System

The present application provides a system including a test unit, where the test unit includes an immune cell line test module, a primary immune cell test module, and a tumor-infiltrating immune cell test module, and may run effectively through a stepped timing sequence; the platform further includes a data acquisition unit, which is configured to respectively record the data run by each module of the test unit; the platform further includes a data assessment unit, which is configured to assess integrate and rank the data recorded by the data acquisition unit.

In the test unit, the immune cell line test module and the primary immune cell test module may respectively include an immune cell line test sub-module and an immune cell line test sub-module, and the data output by the immune cell line test module and the primary immune cell test module may be distinguished and incorporated into different data methods. In a specific embodiment, the test unit and the data acquisition unit can be docked in real time, and the data of the test unit is recorded and classified in time by the data acquisition unit after being output. The data stored by the data acquisition unit is output to a data assessment unit, and the data assessment unit integrates the data based on data characteristics and outputs an agent development risk assessment level index.

Specifically, an analyte input into the test unit will be first input into the immune cell line target cell test sub-module, the effectiveness against the target biological effect will be tested, the output data will be recorded by the data acquisition unit and input into the data assessment unit for level index assessment, and the risk assessment level index of the test is divided into two levels of positive (+) or negative (−) using a dual-level system. Where if the analyte does not pass the assessment of the immune cell line target cell test, i.e. being negative, it will be removed from the system of agent s for tumor immunotherapy and the output data will not be included in subsequent methods for assessment. And if the analytes pass the assessment of the immune cell line target cell test, i.e. being positive, the output data will be incorporated into the data collection unit and recorded and stored.

The data output by the non-target cell module is recorded and stored by the data acquisition unit, and is assessed through integration into the data method using a multi-level system, i.e., outputting a multi-interval scoring level index. The data output by the tumor-infiltrating immune cell test module is recorded and stored by the data acquisition unit, and is assessed through integration into the data method using a multi-level system, i.e., outputting a multi-interval scoring level index. The test data corresponding to each analyte to be tested are integrated by the data acquisition unit, input into the data assessment unit for multi-level index risk assessment to predict and assess the pharmaceutic risk level of the analyte.

In summary, after being input into the platform, all of the analytes can run in three units, namely a test unit, a data acquisition unit, and a data assessment unit. Where, the analytes whose characteristics do not meet the risk assessment dual-level index criteria of the immune cell line target cell test will be removed in time and do not need to be run in all modules of the test unit, thereby improving the operational efficiency of the entire platform. The analytes that pass the immune cell line target cell test will run in three modules of the immune cell line test module, the primary immune cell test module and the tumor-infiltrating immune cell test module in the test unit; the data of the tests are collected and integrated by the data acquisition unit and then input into the data assessment unit, and subjected to the index rating according to a multi-level system method, where the output rating index can be used as a biological activity assessment standard of the analyte to be incorporated into the judgment basis of the pharmaceutic property of the analyte by researchers.

In the present application, an analyte may first run an immune cell line target cell test sub-module; the test and assessment of the other modules in the test unit are then performed only when the analyte passes the assessment of the immune cell line target cell test. While the primary immune cell target cell test sub-module, the immune cell line non-target cell test sub-module, the primary immune cell non-target cell test sub-module, and the tumor-infiltrating immune cell test sub-module may run simultaneously or sequentially; they may run in random order, also may run in a predetermined order. For example, the analyte that passes the immune cell line target cell test may be sequentially input into and run the primary immune cell target cell test sub-module, the immune cell line non-target cell test sub-module, the primary immune cell non-target cell test sub-module, and the tumor-infiltrating immune cell test module; or sequentially input into and run the immune cell line non-target cell test sub-module, the primary immune cell target cell test sub-module, the primary immune cell non-target cell test sub-module, and the tumor-infiltrating immune cell test module. Besides, the data assessment unit may further include a filter element configured to filter an analyte in the test unit corresponding to the data based on the assessment of the data. In a specific case, it can be specified that the analyte passing the immune cell line target cell test firstly run the primary immune cell target cell test sub-module, and only the analyte with a positive (+) assessment result may continue to run and be input into the immune cell line non-target cell test sub-module, the primary immune cell non-target cell test sub-module and the tumor-infiltrating immune cell test module in the platform, with the removal of the analyte with a negative (−) assessment result of the primary immune cell target cell test sub-module from the platform; while the immune cell line non-target cell test sub-module, the primary immune cell non-target cell test sub-module, and the tumor-infiltrating immune cell test sub-module may run simultaneously or sequentially; they may run in random order, also may run in a predetermined order.

In a specific embodiment, a test procedure for an analyte includes the following steps:

firstly, the analyte is preferentially tested in a target cell test sub-module in an immune cell line test module, data of the analyte are assessed after being run by a data acquisition unit and a data assessment unit, where the data assessment unit is assessed by adopting a dual-level method, the analyte assessed as negative (−) will be removed from the platform, and only the analyte assessed as positive (+) will continue to run in the platform.

Secondly, the analyte undergoes a new round of assessment in the target cell test sub-module of the primary immune cell test module, and the data of the analyte are also assessed after being run by the data acquisition unit and the data assessment unit, where the data assessment unit is also assessed by adopting a dual-level method, the analyte assessed as negative (−) may be removed from the platform, and only the analyte assessed as positive (+) may continue to run in the platform.

Subsequently, the analyte will be run in the non-target cell test sub-module of the immune cell line test module, the non-target cell test sub-module of the primary immune cell test module, and the tumor-infiltrating immune cell test module for data collection, respectively, while the data assessment unit may or may not be run temporarily.

And finally, the data acquisition unit integrates the acquired data obtained by the run of the analyte in the test unit, the data are input into the data assessment unit for multi-level system assessment, and the output assessment index can be used for assessing the pharmaceutic property of the analyte on the biological property.

Without intending to be bound by any theory, the following examples are intended merely to illustrate the fusion proteins, methods of preparation, uses, etc., of the present application and are not intended to limit the scope of the present application.

The application comprises the following embodiments:

1. A method of assessing the effect of an analyte on tumor immune cells comprising the steps of: i) assessing the effect of the analyte on target cells, ii) assessing the effect of the analyte on non-target cells; and iii) assessing the effect of the analyte on tumor immune infiltration; wherein the step i) comprises: i-1) assessing the effect of the analyte on an immune cell line target cells, and i-2) assessing the effect of the analyte on primary immune cell target cells; wherein after the assessment of step i-1), the assessment result is divided into two levels of positive (+) and negative (−), and the analyte with a negative assessment result is directly determined as a negative analyte without performing any subsequent steps.

2. The method according to embodiment 1, wherein the step i-2) is continued for the analyte with a positive assessment result in the step i-1), and the assessment result is divided into two levels of positive (+) or negative (−).

3. The method according to embodiment 2, wherein the analyte with a negative assessment result in step i-2) is directly determined as a negative analyte without performing any subsequent steps.

4. The method according to any one of embodiments 1-3, wherein after the assessment of step ii), the assessment result is recorded as a multi-interval scoring level index.

5. The method according to any one of embodiments 1-4, wherein the step ii) comprises assessing the effect of the analyte on immune cell line non-target cells, and/or assessing the effect of the analyte on primary immune cell non-target cells.

6. The method according to any one of embodiments 1-5, wherein after the assessment of step iii), the assessment result is recorded as a multi-interval scoring level index.

7. The method according to any one of embodiments 1-6, wherein the step iii) comprises: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of natural killer cells (NK cells) in tumor tissue.

8. The method according to embodiment 7, wherein the phenotype of T cells comprises: a ratio of the T cells in tumor tissue, the proliferative capacity of the T cells, the activity of the T cells, the expression level of interleukin-2 (IL-2) in the T cells, the expression level of tumor necrosis factor α (TNFα) in the T cells, the expression level of granzyme in the T cells, the expression level of interferon-γ (IFNγ) in the T cells, and/or the expression level of programmed death receptor-1 (PD1) in the T cells.

9. The method according to any one of embodiments 7-8, wherein the phenotype of dendritic cells comprises: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

10. The method according to any one of embodiments 7-10, wherein the phenotype of NK cells comprises: a ratio of the NK cells in tumor tissue, the proliferative capacity of the NK cells, the activity of the NK cells, the expression level of C-type lectin receptor family member A (NKG2A) in the NK cells, the expression level of granzyme in the NK cells, and/or the expression level of killer cell immunoglobulin-like receptor KIR in the NK cells.

11. The method according to embodiment 7, wherein the phenotype of macrophages comprises: a ratio of the macrophages in tumor tissue, the proliferative capacity of the macrophages, the activity of the macrophages, and/or a ratio of M1-type macrophages to M2-type macrophages in tumor tissue.

12. A method of assessing the effect of an analyte on tumor immune cells comprising the steps of: a) assessing the effect of the analyte on B cells, b) assessing the effect of the analyte on non-target cells; and c) assessing the effect of the analyte on tumor immune infiltration; wherein step a) comprises: a-1) assessing the effect of the analyte on B cells of an immune cell line, and a-2) assessing the effect of the analyte on B cells of primary immune cells; wherein the assessment result is divided into two levels of positive (+) and negative (−), and the analyte with a negative assessment result is directly determined as a negative analyte without performing any subsequent steps.

13. The method according to embodiment 12, wherein the step a) comprises: assessing the effect of the analyte on the proliferative capacity of the B cells, assessing the effect of the analyte on the expression level of IL-6 in the B cells, and/or assessing the effect of the analyte on the level of antibody produced by the B cells.

14. The method according to any one of embodiments 12-13, wherein the non-target cells comprise T cells, macrophages, dendritic cells, and/or NK cells.

15. The method according to any one of embodiments 12-14, wherein the step b) comprises: assessing the effect of the analyte on the phenotype of T cells, assessing the effect of the analyte on the phenotype of dendritic cells, assessing the effect of the analyte on the phenotype of macrophages, and/or assessing the effect of the analyte on the phenotype of NK cells.

16. The method according to embodiment 15, wherein the phenotype of T cells comprises: the expression level of cytokine IL-2 in the T cell, the expression level of IFNγ in the T cell, and/or the proliferative capacity of the T cell.

17. The method according to any one of embodiments 15-16, wherein the phenotype of dendritic cells comprises: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells.

18. The method according to any one of embodiments 15-17, wherein the phenotype of NK cells comprises: the proliferative capacity and the activity of the NK cells, the expression level of NKG2A in the NK cells, the expression level of granzyme in the NK cells, and/or the expression level of KIR in the NK cells.

19. The method according to any one of embodiments 15-18, wherein the phenotype of macrophages comprises: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

20. The method according to any one of embodiments 12-19, wherein the step c) comprises: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue.

21. The method according to embodiment 20, wherein the phenotype of T cells comprises: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells.

22. The method according to any one of embodiments 20-21, wherein the phenotype of dendritic cells comprises: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

23. The method according to any one of embodiments 20-22, wherein the phenotype of NK cells comprises: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells.

24. The method according to any one of embodiments 20-23, wherein the phenotype of macrophages comprises: a ratio of the macrophages in tumor tissue, the proliferative capacity of the macrophages, the activity of the macrophages, and/or a ratio of M1-type macrophages to M2-type macrophages in tumor tissue.

25. A method of assessing the effect of an analyte on tumor immune cells comprising the steps of: a') assessing the effect of the analyte on T cells, b') assessing the effect of the analyte on non-target cells; and c') assessing the effect of the analyte on tumor immune infiltration; wherein the step a') comprises: a-1') assessing the effect of the analyte on T cells of an immune cell line, and a-2') assessing the effect of the analyte on T cells of primary immune cells; wherein the assessment result is divided into two levels of positive (+) and negative (−), and the analyte with a negative assessment result is directly determined as a negative analyte without performing any subsequent steps.

26. The method according to embodiment 25, wherein the step a') comprises: assessing the effect of the analyte on the expression level of IL-2 in the T cells, assessing the effect of the analyte on the expression level of IFNγ in the T cells, and/or assessing the effect of the analyte on the cell the proliferative capacity of the T cells.

27. The method according to any one of embodiments 25-26, wherein the non-target cells comprise B cells, macrophages, dendritic cells, and/or NK cells.

28. The method according to any one of embodiments 25-27, wherein the step b') comprises: assessing the effect of the analyte on the phenotype of B cells, assessing the effect of the analyte on the phenotype of dendritic cells, assessing the effect of the analyte on the phenotype of macrophages, and/or assessing the effect of the analyte on the phenotype of NK cells.

29. The method according to embodiment 28, wherein the phenotype of B cells comprises: the proliferative capacity of the B cells, and/or production of antibodies by the B cells.

30. The method according to any one of embodiments 28-29, wherein the phenotype of dendritic cells comprises: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells.

31. The method according to any one of embodiments 28-30, wherein the phenotype of NK cells comprises: the proliferative capacity and the activity of the NK cells, and the expression level of NKG2A in the NK cells, the expression level of granzyme in the NK cells, and/or the expression level of KIR in the NK cells.

32. The method according to any one of embodiments 28-31, wherein the phenotype of macrophages comprises: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

33. The method according to any one of embodiments 28-32, wherein the step c') comprises: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue.

34. The method according to embodiment 33, wherein the phenotype of T cells comprises: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells.

35. The method according to any one of embodiments 33-34, wherein the phenotype of dendritic cells comprises: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells.

36. The method according to any one of embodiments 33-35, wherein the phenotype of NK cells comprises: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells.

37. The method according to any one of embodiments 33-36 wherein the phenotype of macrophages comprises: a ratio of the macrophages in tumor tissue, the proliferative capacity of the macrophages, the activity of the macrophages, and/or a ratio of M1-type macrophages to M2-type macrophages in tumor tissue.

38. A system comprising a test unit, a data acquisition unit, and a data assessment unit; wherein the test unit comprises an immune cell line test module S1, a primary immune cell test module S2, and a tumor-infiltrating immune cell test module S3; the data acquisition unit is configured to independently record the data generated by each module of the test unit respectively; and the data assessment unit is configured to assess the data recorded by the data acquisition unit.

39. The system according to embodiment 38, wherein the data assessment unit further comprises a filter element configured to filter an analyte in the test unit corresponding to the data based on the assessment of the data.

40. The system according to any one of embodiments 38-39, wherein the immune cell line test module S1 comprises an immune cell line target cell test sub-module S1-1 and an immune cell line non-target cell test sub-module S1-2.

41. The system according to embodiment 40, wherein the data assessment unit is configured to assess the input data of the sub-module S1-1 recorded by the data acquisition unit, and output an assessment result of a positive (+) or negative (−) level.

42. The system according to embodiment 41, wherein the filter element is configured to remove the analyte corresponding to the data with a negative assessment result of the sub-module S1-1 from the test unit.

43. The system according to any one of embodiments 38-42, wherein the primary immune cell test module S2 comprises a primary immune cell target cell test sub-module S2-1 and a primary immune cell non-target cell test sub-module S2-2.

44. The system according to embodiment 43, wherein the data assessment unit is configured to assess the input data of the sub-module S2-1 recorded by the data acquisition unit, and output an assessment result of a positive (+) or negative (−) level.

45. The system according to embodiment 44, wherein the filter element is configured to remove the analyte corresponding to the data with a negative assessment result of the sub-module S2-1 from the test unit.

46. The system according to any one of embodiments 38-45, wherein the data assessment unit is configured to assess the data of the module S1, the data of the module S2, and the data of the module S3 recorded by the input data acquisition unit, and output a multi-interval scoring level index.

47. The system according to embodiment 46, wherein the data assessment unit is configured to assess and predict an agent development risk based on the level index.

48. Use of the system according to any one of embodiments 38-47 in the preparation of a high throughput screening system of agents for tumor immunotherapy.

49. A method of assessing the effectiveness and/or safety of agents for tumor immunotherapy against tumor immune cells, comprising the steps of using the system according to any one of embodiments 38-47.

Reagent and Material Information

TABLE 1

Reagent Art. No. and manufacturer information

| Reagent | Manufacturer | Art. No. |
| --- | --- | --- |
| CellTiter-Glo ® Luminescent Cell Viability Assay | Promega | G7573 |
| PMI 1640 | BI | 01-100-1ACS |
| DMEM | Gibico | C11965500BT |
| FBS | BI | 04-002-1A |
| FBS | Gibco | 10091-148 |
| BSA | amresco | 0332-1KG |
| PBS | BI | 02-024-1ACS |
| Tween-20 | Solarbio | T8220 |
| anti-CD3 antibody | Invitrogen | 16-0037-85 |
| Anti-CD28 antibody | Invitrogen | 16-0289-85 |
| DMSO | RNBJ1732 | Sigma-Aldrich |
| Human IL-2 DuoSet ELISA | R&D | DY202 |
| mGM-CSF | Sinobiologic | 51048-MNAH |
| mIL-4 | Sinobiologic | 51084-MNAE |
| PE-Cy ™7 Hamster Anti-Mouse CD11c | BD Bioscience | 558079 |
| Ms CD335 (NKP46) BV421 | BD Pharmingen | 562850 |
| F4/80 PE T45-2342 | BD Pharmingen | 565410 |
| CD3e Monoclonal Antibody (145-2C11), PE | eBioscience | 12-0031-82 |

TABLE 2

Instrument Specification Number and manufacturer information

| Instrument | Model | Brand |
| --- | --- | --- |
| Carbon dioxide incubator | 3111 | Thermo Fisher Scientific |
| Multifunctional plate reader | SpectraMax i3x | Molecular Devices |
| Biological safety cabinet | BSC-1600 II A2 | Suzhou Antai Airtech Co., Ltd. |
| Ultrapure water instrument | Simplicity | Millipore |
| Countstar automatic cell counter | IC 1000 | Shanghai Ruiyu Biotech Co., Ltd. |
| Flow cytometer | BD LSRFortessa | Becton, Dickinson and Company |

TABLE 3

Cell types/batch numbers and manufacturer information

| Cell | Types/batch number | Company |
| --- | --- | --- |
| Jurkat E6-1 | Human Acute T cell Leukemia | Cell Bank, Chinese Academy of Sciences |
| THP1 | Human Acute monocytic Leukemia | Cell Bank, Chinese Academy of Sciences |
| MC38 | Mice colon adenocarcinoma cells | Shanghai Medicilon Inc. |
| Human PBMC cell | NPB-MNC/LP200511 | AllCells Biotechnology (Shanghai) Co., Ltd |

TABLE 4

Mouse source and manufacturer information

| Strain | Week-old | Company |
| --- | --- | --- |
| C57BL/6 | 6-8 weeks | Shanghai SLAC Laboratory Animal Co., Ltd. |
| BALB/C | 6-8 weeks | Shanghai SLAC Laboratory Animal Co., Ltd. |

Examples

The target cells against the analytes A, B, C, and D used in this Example are T lymphocytes. Therefore, the used immune cell line target cells-Jurkat cells are human-derived T lymphocyte leukemia cells, and the analyzed primary target cells are T cells in human peripheral blood mononuclear cells (PBMC).

1. Immune Cell Line Target Cell Test Sub-Module

Firstly, a biological function test of immune cell line target cells was performed on analytes A, B, C, and D, where the steps were as follows:

1.1 Analytes A, B, C, and D powders were dissolved in DMSO to 10 mM, 2 µl of each analyte was added to 998 µl of 1640 medium (RPMI 1640 plus 10% FBS as mentioned), and mixed thoroughly as a first concentration point via vortex oscillation. The analyte solutions were gradually diluted 3-fold with 0.2% DMSO medium for a total of 8 concentration points.

1.2 Jurkat cells were harvested, the cell density was adjusted to $1.1 \times 10^6$/ml with 1640 medium, 120 µl of cell suspension and 120 µl of analyte solution were taken from each well, followed by incubation for 1 h in a cell incubator.

1.3 Anti-CD28 and anti-CD3 antibodies were diluted to 10 µg/ml in 1640 medium, 20 µl of 1640 medium was added to each well (20 µl of 1640 medium was added to control wells), and 180 µl of analyte and cell mixture (mixed thoroughly before addition) were added to the plate. The cells were incubated for 24 h in a cell incubator and centrifuged, and the supernatant was taken from each well for later use.

1.4. The level of the cytokine IL-2 in the cell supernatant was detected by an ELISA detection reagent to determine the biological effects of the analytes on the target cell line Jurkat cells, and the data was collected into an assessment system to perform dual-level method assessment.

Results: analyte A had a test index of negative (−) rating and analytes B, C, and D had positive (+) rating, so analyte A was removed, and analytes B, C, and D were subjected to primary immune cell target cell testing.

2. Primary Immune Cell Target Cell Test Sub-Module

Then, biological function tests of primary immune cell target cells were carried out on the analytes B, C, and D, and the steps were as follows:

2.1 2 µl of each of 10 mM analytes B, C, and D were added to 998 µl of 1640 medium and mixed thoroughly as a first concentration point via vortex oscillation. The analyte solutions were gradually diluted 3-fold with 0.2% DMSO medium for a total of 8 concentration points.

1.2 PBMC cells were harvested, the cell density was adjusted to $1.1 \times 10^6$/ml with 1640 medium, 120 µl of cell suspension and 120 µl of analyte solution were taken from each well, followed by incubation for 1 h in a cell incubator.

2.3 Anti-CD28 and anti-CD3 antibodies were respectively diluted to 10 µg/ml and 0.1 g/ml in 1640 medium, 20 µl of 1640 medium was added to each well (20 µl of 1640 medium was added to control wells), and 180 µl of analyte and cell mixture were added to the plate. The cells were incubated for 24 h in a cell incubator and centrifuged, and the supernatant was taken from each well for later use.

2.4. The level of the cytokine IL-2 in the cell supernatant was detected by an ELISA detection reagent to determine the biological effects of the analytes on the T cell primary target cells, and the data was collected into an assessment system to perform dual-level method assessment.

Results: analyte B had a test index of negative (−) rating and analytes C and D had positive (+) rating, so analyte B was removed. The analytes C and D are subjected to biological function tests on a non-target cell test unit in an immune cell line test module, a non-target cell test unit in a primary immune cell test module and a tumor-infiltrating immune cell test module.

3. Immune Cell Line Non-Target Cell Test and Primary Immune Cell Non-Target Cell Test Then, biological function tests of non-target cells were carried out on the analytes C and D. In this example, the non-target cell assay focused on the cytotoxicity of the analyte, and the cell viability assay was performed using CTG cell viability assay reagents. The immune cell line non-target cells in this example used the human acute leukemia monocytic cell line THP1, and the primary cell non-target cells were mouse bone marrow-derived dendritic cells (BMDC).

3.1 2 µl of 10 mM analytes C, and D were added to 998 µl of 1640 medium and mixed thoroughly as a first concentration point via vortex oscillation. The analyte solutions were gradually diluted 2-fold with 0.2% DMSO medium for a total of 8 concentration points.

3.2 THP1 and BMDC were harvested, the cell density was adjusted to 1 million/ml with 1640 medium, 100 µl of cell suspension and 100 µl of analyte solution were taken from each well, followed by incubation for 24 h in a cell incubator.

3.3 The above-mentioned non-target cells were cultured in a cell incubator for 24 h, followed by centrifuging and removing 100 µl of supernatant from each well, 25 µl of CTG detection solution was added to each well, followed by standing in the dark for 15 min at room temperature, reading values by using a multifunctional reader, and recording data by using a data acquisition unit.

4 Tumor-Infiltrating Immune Cell Test Module

Finally, analytes B, C, and D were subjected to tumor-infiltrating immune cells test. The in-situ tumor formed by subcutaneous inoculation of mouse colon cancer cell line MC38 cells was isolated and cultured in vitro, meanwhile, different doses of analytes were added for treatment, and then the biological effect of the analytes was assessed by analyzing the characteristics of the infiltrated immune cells.

4.1 MC38 cells cultured in vitro were harvested, resuspended in PBS buffer and adjusted to 5 million/ml, then inoculated subcutaneously in the abdomen of 6-8 week old C57BL/6 mice, with an amount of 100 µl per mouse.

4.2 The tumor was stripped when the tumor grows to 500-1000 $mm^3$, the milled cells were adjusted to $10^7$/ml by using 1640 culture medium for later use, 2 µl of 10 mM analytes C and D were added into 998 µl of 1640 culture medium and mixed thoroughly as a first concentration point via vortex oscillation. The analyte solutions were diluted 2-fold with 0.2% DMSO medium for a total of 6 concentration points, and 100 µl of the cell suspension and 100 µl of the analyte solution were taken from each well, followed by incubation for 24 h in a cell incubator using 0.10% DMSO medium as a control group.

4.3 Cells were harvested, and the proportion and survival of T cells (CD3+), dendritic cells (DC, CD11c+), macrophages (Mac, F4/80+), and NK cells (NKp46+) cells in the cells were analyzed using a flow cytometer, indicating the biological effect of the analytes in tumor-infiltrating immune cells.

4.4 The data acquisition unit integrated all recorded data and input a data method, and the data method output the level indexes of the C and D analytes according to the multi-interval scoring level index assessment system.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of screening an agent for tumor immunotherapy, comprising assessing the effect of an analyte on tumor immune cells, the method comprises the steps of:
   i) assessing the effect of the analyte on target cells, when the target cells are T cells;

ii) assessing the effect of the analyte on non-target cells; and iii) assessing the effect of the analyte on tumor immune infiltration;

wherein step i) comprises:

i-1) assessing the effect of the analyte on the proliferative capacity of immune cell line target cells, and i-2) assessing the effect of the analyte on the IL-2 expression level of primary immune cell target cells;

wherein after the assessment of step i-1), the assessment result is divided into two levels of positive (+) and negative (−), and the analyte with a negative assessment result is directly determined as a negative analyte without performing any subsequent steps;

step i-2) is continued for the analyte with a positive assessment result in the step i-1), and the assessment result is divided into two levels of positive (+) or negative (−); the analyte with a negative assessment result in step i-2) is directly determined as a negative analyte without performing any subsequent steps;

step ii) comprises assessing the effect of the analyte on the cell viability of immune cell line non-target cells, and/or assessing the effect of the analyte on the cell viability of primary immune cell non-target cells, iv) determining the analyte with a level of positive (+) assessment after step i-2) as the agent for tumor immunotherapy.

2. The method according to claim 1, wherein after the assessment of step ii), the assessment result is recorded as a multi-interval scoring level index.

3. The method according to claim 1, wherein after the assessment of step iii), the assessment result is recorded as a multi-interval scoring level index.

4. The method according to claim 1, wherein the step iii) comprises: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of natural killer cells (NK cells) in tumor tissue.

5. The method according to claim 4, wherein the phenotype of T cells comprises: a ratio of the T cells in tumor tissue, the proliferative capacity of the T cells, the activity of the T cells, the expression level of interleukin-2 (IL-2) in the T cells, the expression level of tumor necrosis factor α (TNFα) in the T cells, the expression level of granzyme in the T cells, the expression level of interferon-γ (IFNγ) in the T cells, and/or the expression level of programmed death receptor-1 (PD1) in the T cells;

wherein the phenotype of dendritic cells comprises: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells;

wherein the phenotype of NK cells comprises: a ratio of the NK cells in tumor tissue, the proliferative capacity of the NK cells, the activity of the NK cells, the expression level of C-type lectin receptor family member A (NKG2A) in the NK cells, the expression level of granzyme in the NK cells, and/or the expression level of killer cell immunoglobulin-like receptor KIR in the NK cells; and/or wherein the phenotype of macrophages comprises: a ratio of the macrophages in tumor tissue, the proliferative capacity of the macrophages, the activity of the macrophages, and/or a ratio of M1-type macrophages to M2-type macrophages in tumor tissue.

6. A method of screening an agent for tumor immunotherapy, comprising assessing the effect of an analyte on tumor immune cells, the method comprises the steps of:

a) assessing the effect of the analyte on target cells, the target cells are B cells, b) assessing the effect of the analyte on non-target cells; and c) assessing the effect of the analyte on tumor immune infiltration;

wherein step a) comprises:

a-1) assessing the effect of the analyte on B cells of an immune cell line, and a-2) assessing the effect of the analyte on B cells of primary immune cells;

wherein the assessment result is divided into two levels of positive (+) and negative (−), and the analyte with a negative assessment result is directly determined as a negative analyte without performing any subsequent steps, step a-2) is continued for the analyte with a positive assessment result in the step a-1), and the assessment result is divided into two levels of either positive (+) or negative (−); the analyte with a negative assessment result in step a-2) is directly determined as a negative analyte without performing any subsequent steps;

step b) comprises assessing the effect of the analyte on immune cell line non-target cells, and/or assessing the effect of the analyte on primary immune cell non-target cells, d) determining the analyte with a level of positive (+) after step a-2) as the agent for tumor immunotherapy.

7. The method according to claim 6, wherein the step a) comprises: assessing the effect of the analyte on the proliferative capacity of the B cells, assessing the effect of the analyte on the expression level of IL-6 in the B cells, and/or assessing the effect of the analyte on the level of antibody produced by the B cells;

wherein the non-target cells comprise T cells, macrophages, dendritic cells, and/or NK cells.

8. The method according to claim 6, wherein the step b) comprises: assessing the effect of the analyte on the phenotype of T cells, assessing the effect of the analyte on the phenotype of dendritic cells, assessing the effect of the analyte on the phenotype of macrophages, and/or assessing the effect of the analyte on the phenotype of NK cells;

wherein the phenotype of T cells comprises: the expression level of cytokine IL-2 in the T cell, the expression level of IFNγ in the T cell, and/or the proliferative capacity of the T cell;

wherein the phenotype of dendritic cells comprises: the proliferative capacity and the activity of the dendritic cells, the expression levels of the co-stimulatory molecules CD80 and CD86 in the dendritic cells, and the expression level of IL-12 in the dendritic cells, the expression level of type I interferon in the dendritic cells, and/or the expression level of IL-6 in the dendritic cells;

wherein the phenotype of NK cells comprises: the proliferative capacity and the activity of the NK cells, the expression level of NKG2A in the NK cells, the expression level of granzyme in the NK cells, and/or the expression level of KIR in the NK cells; and/or wherein the phenotype of macrophages comprises: the proliferative capacity and the activity of the macrophages, a ratio of M1-type macrophages to M2-type macrophages, the expression level of co-stimulatory molecules CD80 and CD86 in the macrophages, and/or the expression level of type I interferon produced in the macrophages.

9. The method according to claim 6, wherein the step c) comprises: assessing the effect of the analyte on the phenotype of T cells in tumor tissue, assessing the effect of the analyte on the phenotype of dendritic cells in tumor tissue, assessing the effect of the analyte on the phenotype of macrophages in tumor tissue, and/or assessing the effect of the analyte on the phenotype of NK cells in tumor tissue;

wherein the phenotype of T cells comprises: a ratio of the T cells in tumor tissue, the proliferative capacity of the T cells, the activity of the T cells, the expression level of IL-2 in the T cells, the expression level of TNFα in the T cells, the expression level of granzyme in the T cells, the expression level of IFNγ in the T cells, and/or the expression level of PD1 in the T cells;

wherein the phenotype of dendritic cells comprises: a ratio of the dendritic cells in tumor tissue, the proliferative capacity of the dendritic cells, the activity of the dendritic cells, the expression level of co-stimulatory molecules CD80 and CD86 in the dendritic cells, and/or the expression level of PD-L1 in the dendritic cells;

wherein the phenotype of NK cells comprises: a ratio of the NK cells in tumor tissue, the proliferative capacity of the NK cells, the activity of the NK cells, the expression level of NKG2A in the NK cells, the expression level of granzyme in the NK cells, and/or the expression level of KIR in the NK cells;

wherein the phenotype of macrophages comprises: a ratio of the macrophages in tumor tissue, the proliferative capacity of the macrophages, the activity of the macrophages, and/or a ratio of M1-type macrophages to M2-type macrophages in tumor tissue.

* * * * *